United States Patent
Auriol et al.

(10) Patent No.: US 9,907,760 B2
(45) Date of Patent: Mar. 6, 2018

(54) COSMETIC AND PHARMACEUTICAL COMPOSITION COMPRISING N-ACETYLGLUCOSAMINE-6-PHOSPHATE

(75) Inventors: Daniel Auriol, Toulouse (FR); Fabrice Lefevre, Auterive (FR); Renaud Nalin, Dremil-Lafage (FR); Gerard Redziniak, Antony (FR)

(73) Assignee: LIBRAGEN, Toulouse (FR)

( * ) Notice: Subject to any disclaimer, the term of this patent is extended or adjusted under 35 U.S.C. 154(b) by 524 days.

(21) Appl. No.: 13/637,031

(22) PCT Filed: Apr. 1, 2011

(86) PCT No.: PCT/FR2011/050732
§ 371 (c)(1),
(2), (4) Date: Sep. 25, 2012

(87) PCT Pub. No.: WO2011/121250
PCT Pub. Date: Oct. 6, 2011

(65) Prior Publication Data
US 2013/0012475 A1 Jan. 10, 2013

(30) Foreign Application Priority Data
Apr. 2, 2010 (FR) .................................... 10 52536

(51) Int. Cl.
| A61K 31/7008 | (2006.01) |
| A61K 8/60 | (2006.01) |
| A61K 8/67 | (2006.01) |
| A61K 31/07 | (2006.01) |
| A61K 31/11 | (2006.01) |
| A61K 31/192 | (2006.01) |
| A61K 31/203 | (2006.01) |
| A61K 31/232 | (2006.01) |
| A61Q 19/08 | (2006.01) |
| A61Q 1/14 | (2006.01) |

(52) U.S. Cl.
CPC ............... *A61K 31/07* (2013.01); *A61K 8/60* (2013.01); *A61K 8/671* (2013.01); *A61K 31/11* (2013.01); *A61K 31/192* (2013.01); *A61K 31/203* (2013.01); *A61K 31/232* (2013.01); *A61K 31/7008* (2013.01); *A61Q 19/08* (2013.01); *A61Q 1/14* (2013.01)

(58) Field of Classification Search
CPC .......... A61K 8/60; A61K 8/671; A61K 31/07; A61K 31/11; A61K 31/203; A61K 31/232; A61K 31/7008; A61K 31/192; A61Q 19/08; A61Q 1/14
USPC ..................................... 514/62; 536/53, 55.2
See application file for complete search history.

(56) References Cited

U.S. PATENT DOCUMENTS

| 5,759,556 | A | * | 6/1998 | Burger et al. ................. 424/401 |
| 2002/0119952 | A1 | | 8/2002 | Petrus |
| 2003/0114418 | A1 | * | 6/2003 | Pulaski et al. .................. 514/62 |
| 2004/0131693 | A1 | * | 7/2004 | Postmes et al. ............... 424/539 |
| 2007/0281009 | A1 | | 12/2007 | Kamisono et al. |
| 2008/0020997 | A1 | | 1/2008 | Capomacchia et al. |
| 2008/0160110 | A1 | * | 7/2008 | Kang et al. .................... 424/725 |

FOREIGN PATENT DOCUMENTS

| EP | 1 384 482 | 1/2004 |
| EP | 1 917 956 | 5/2008 |
| GB | 896 940 | 5/1962 |
| KR | 10-2006-0008155 | 1/2006 |
| WO | WO 2006/006757 | 1/2006 |

OTHER PUBLICATIONS

Written Opinion in International Application No. PCT/FR2011/050732, Sep. 30, 2011, pp. 1-7.

* cited by examiner

*Primary Examiner* — Michael C Henry
(74) *Attorney, Agent, or Firm* — Saliwanchik, Lloyd & Eisenschenk

(57) ABSTRACT

The present invention relates to a cosmetic or pharmaceutical composition comprising N-acetylglucosamine-6-phosphate or a salt thereof and, optionally, a compound of the vitamin A family, and also to a device containing same.

16 Claims, 4 Drawing Sheets

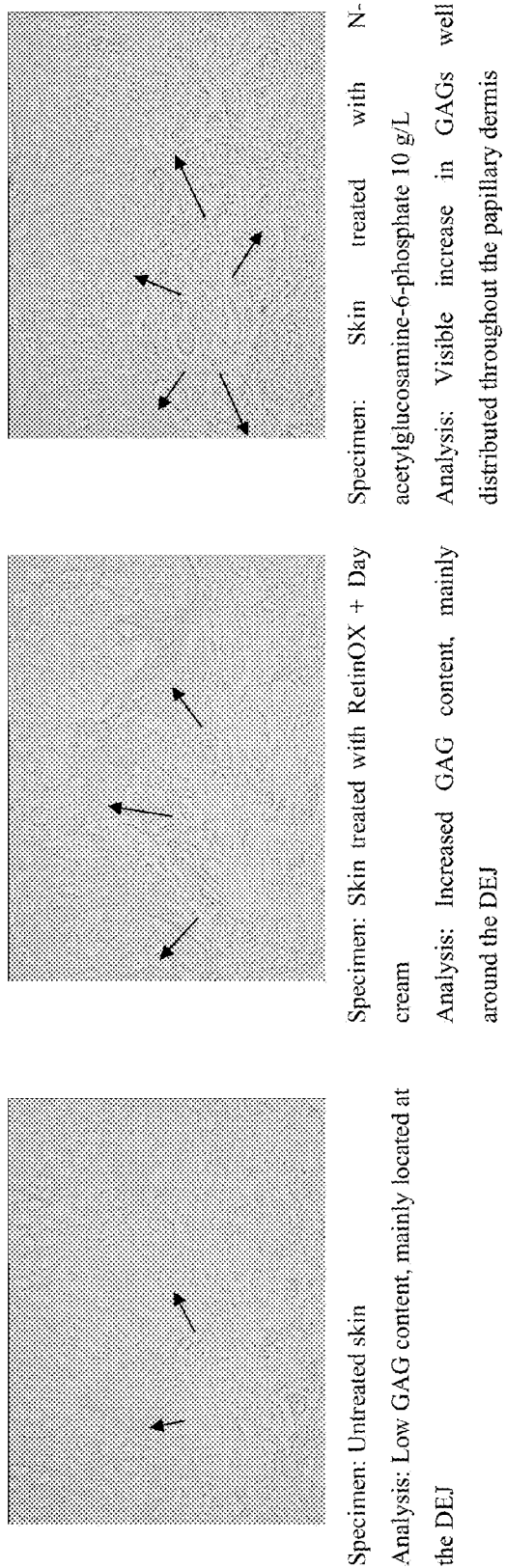

ANALYSIS OF GLYCOSAMINOGLYCAN PRODUCTION IN SKIN AFTER 6 DAYS OF TREATMENT WITH N-ACETYLGLUCOSAMINE-6-PHOSPHATE

Specimen: Untreated skin
Analysis: Low GAG content, mainly located at the DEJ

Specimen: Skin treated with RetinOX + Day cream
Analysis: Increased GAG content, mainly around the DEJ Specimen: Skin treated with N-acetylglucosamine-6-phosphate 10 g/L
Analysis: Visible increase in GAGs well distributed throughout the papillary dermis Abbreviations: GAG: glycosaminoglycans
DEJ: dermal-epidermal junction

FIGURE 3

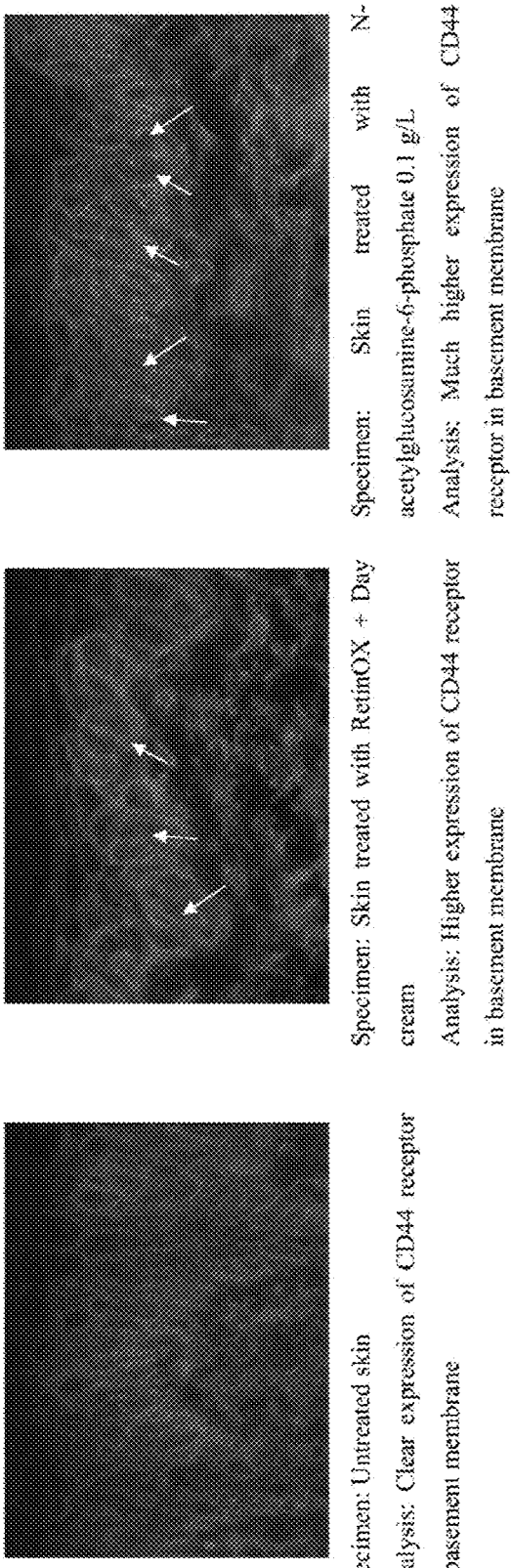

US 9,907,760 B2

COSMETIC AND PHARMACEUTICAL COMPOSITION COMPRISING N-ACETYLGLUCOSAMINE-6-PHOSPHATE

CROSS-REFERENCE TO RELATED APPLICATION

This application is the U.S. national stage application of International Patent Application No. PCT/FR2011/050732, filed Apr. 1, 2011, the disclosure of which is hereby incorporated by reference in its entirety, including all figures, tables and amino acid or nucleic acid sequences.

FIELD OF THE INVENTION

The present invention relates to the fields of cosmetics and therapeutics.

CONTEXT OF THE INVENTION

D-glucosamine (glucosamine) is an amino sugar and an important precursor in the biochemical synthesis of glycosylated proteins and lipids. It is commonly used in the treatment of osteoarthritis although its therapeutic effectiveness has not been universally accepted. Glucosamine is believed to promote cartilage formation and repair. A three-year, double-blind clinical trial in 212 patients with osteoarthritis, published in 2001 (Reginster et al., 2001, Lancet, 357, 251-6), reported a 20-25% improvement in symptoms in the glucosamine group versus a slight worsening in the placebo group. Radiographs of the knee showed significant joint space narrowing (a sign of disease progression) for half the patients taking glucosamine.

D-N-acetylglucosamine (N-acetylglucosamine) is a glucosamine derivative with better stability. Glucosamine and N-acetylglucosamine are key metabolites in biochemical processes and are present in structural polymers in humans and animals. Among said polymers, glycosaminoglycans are long unbranched polysaccharides consisting of a repeating disaccharide unit. The repeating unit is a hexose (six-carbon sugar) or a hexuronic acid, linked to a hexosamine (six-carbon sugar containing nitrogen such as N-acetylglucosamine). Examples of glycosaminoglycans are chondroitin sulfate (elastic cartilage, hyaline cartilage, bone, dermis, stratum corneum), dermatan sulfate (dermis, tendon, ligament, fibrocartilage), keratan sulfate (cartilage, stratum corneum), hepain/heparan sulfate (liver, lung, aorta) and hyaluronan (skin).

Glycosaminoglycans form an important component of connective tissue and can account for up to 30% of organic matter. Glycosaminoglycan chains may be covalently linked to a protein to form proteoglycans. Due to the density of the sugar subunits and their charges attracting anions, water sticks to glycosaminoglycans, thereby giving tissues an increased resistance to pressure. Examples of glycosaminoglycan uses include heparin as an anticoagulant, chondroitins which can be found in connective tissues, cartilage and tendons, and hyaluronan which is a component of the extracellular structure of the skin and the synovial fluid lubricant in joints.

By virtue of their mechanical, structural and physiological functions, glycosaminoglycans are important polymers for life and the regulation of their metabolism is an important factor in human and animal health. Thus, there is a constant need for compositions allowing the modulation of glycosaminoglycan production.

In an interesting manner, N-acetylglucosamine has been used for different applications in the field of health and cosmetics for its ability to stimulate hyaluronan synthesis. N-acetylglucosamine is produced either by acid hydrolysis of chitin contained in shrimp and crab shells, or by fermentation (at least with respect to glucosamine which can then be acetylated). Patent application US2008/0020997 discloses a topical formulation of N-acetylglucosamine.

N-acetylglucosamine-6-phosphate is a C6-phosphorylated form of N-acetylglucosamine. N-acetylglucosamine-6-phosphate has been shown to be an intermediate in the synthesis of glycosaminoglycans such as hyaluronan. In this specific pathway, N-acetylglucosamine-6-phosphate is isomerized to N-acetyl-glucosamine-1-phosphate before being activated to UDP-N-acetylglucosamine and incorporated in the polymer (see FIG. 1). N-acetylglucosamine-6-phosphate is therefore an intermediate metabolite which is produced in cells (endogenous compound) and which is not synthesized in order to be excreted in the pericellular space. It further appears that N-acetylglucosamine-6-phosphate is not produced by mammalian cells directly from N-acetylglucosamine.

Phosphorylated sugars are well known high energy compounds used by cells at the crossroads of several metabolic pathways. Most of these phosphorylated sugars are transient compounds continuously recycled by cells, such as glucose-6-phosphate and fructose-6-phosphate. Being an intermediate metabolite in cells, phosphorylated sugars are difficult to isolate in sufficient amounts at reasonable cost to allow them to be tested. Moreover, phosphorylated sugars are unstable and are rapidly hydrolyzed by cellular and bacterial phosphatases into their corresponding non-phosphorylated sugars, thereby precluding their direct use.

Although a single document GB 896940 from 1962 mentions the use of N-acetylglucosamine-6-phosphate among the derivatives of N-acetylglucosamine to promote wound healing (without providing any experimental data on this compound), to our knowledge there is no document in the public domain or accessible to the scientific community which describes the evaluation of N-acetylglucosamine-6-phosphate for these potential therapeutic or cosmetic effects.

Thus, there remains a constant need to develop cosmetic and pharmaceutical compositions modulating the production of glycosaminoglycans and their range of use is quite vast.

SUMMARY OF THE INVENTION

The inventors disclose surprising and unexpected properties of N-acetylglucosamine-6-phosphate as exogenous compound on human cells, notably with respect to glycosaminoglycan production, thereby demonstrating its usefulness in pharmaceutical, veterinary and cosmetic compositions, alone or in combination with other compounds, in particular a compound of the vitamin A family, in order to promote beneficial effects on health and esthetics. The inventors also demonstrate a synergistic effect of the combination of N-acetylglucosamine-6-phosphate and a compound of the vitamin A family.

The present invention therefore relates to the use of a cosmetic composition comprising N-acetylglucosamine-6-phosphate or a cosmetically acceptable salt thereof and, optionally, a compound of the vitamin A family, to treat dry skin or to treat or prevent aging of the skin or the appendages, in particular to treat or prevent wrinkles, in particular deep wrinkles and/or fine lines, to improve skin elasticity and/or tone, to tighten the skin, and/or to regenerate/strengthen the dermal-epidermal junction and/or to enhance skin cell proliferation (in particular keratinocytes and fibroblasts) and/or to enhance the synthesis of structural macromolecules (in particular hyaluronan and/or collagen).

More particularly, the present invention relates to a cosmetic composition comprising N-acetylglucosamine-6-phosphate or a cosmetically acceptable salt thereof. It may additionally comprise a compound of the vitamin A family, preferably selected from the group consisting of retinol, retinal or retinaldehyde (cis or trans), retinoic acid, isotretinoin, adapalene, tretinoin, the salts and derivatives thereof and the mixture thereof. In a still more preferred embodiment, the compound of the vitamin A family is retinol, a salt, an alcohol or an ester thereof. Said composition may be suitable for administration by the topical, oral or injectable route (in particular suitable for intraepidermal and/or intradermal and/or transdermal and/or subcutanous injection and/or micro-injection).

The present invention also relates to a pharmaceutical or veterinary composition comprising N-acetylglucosamine-6-phosphate or a pharmaceutically acceptable salt thereof for use in the treatment of psoriasis, atopic dermatitis, eczema, joint disorders, disorders related to cartilage deficiency, synovial effusions, for modulation of the inflammatory response, for viscosupplementation, and in treatments associated with surgical or postoperative interventions, in particular of the eye, skin and abdomen, preferably of the eye. Preferably, it may additionally comprise a compound of the vitamin A family, preferably selected from the group consisting of retinol, retinal or retinaldehyde (cis or trans), retinoic acid, isotretinoin, adapalene, tretinoin, the salts and derivatives thereof and the mixture thereof. In a still more preferred embodiment, the compound of the vitamin A family is retinol, a salt or an alcohol or an ester thereof. Said composition may be suitable for administration by the topical, oral or injectable route (in particular suitable for intraepidermal and/or intradermal and/or transdermal and/or subcutaneous and/or intramuscular and/or intravenous and/or micro-injection and/or intra-articular injection).

The present invention also relates to a pharmaceutical or veterinary composition comprising N-acetylglucosamine-6-phosphate or a pharmaceutically acceptable salt thereof and a compound of the vitamin A family, preferably selected from the group consisting of retinol, retinal or retinaldehyde (cis or trans), retinoic acid, isotretinoin, adapalene, tretinoin, the salts and derivatives thereof and the mixture thereof. In a still more preferred embodiment, the compound of the vitamin A family is retinol, a salt or an alcohol or an ester thereof. The invention relates to a composition according to this embodiment for the repair and/or regeneration of damaged tissues.

The present invention relates to the use of N-acetylglucosamine-6-phosphate or a pharmaceutically acceptable salt thereof, optionally in combination with a compound of the vitamin A family, for preparing a pharmaceutical or veterinary composition or a medicament for use in the treatment of psoriasis, atopic dermatitis, eczema, joint disorders, disorders related to cartilage deficiency, synovial effusions, for modulation of the inflammatory response, for viscosupplementation, and in treatments associated with surgery, in particular of the eye and abdomen, preferably of the eye. When N-acetylglucosamine-6-phosphate or a salt thereof is not combined in the composition or medicament with a compound of the vitamin A family, then said use may take place in combination with a compound of the vitamin A family. The present invention also relates to a product comprising N-acetylglucosamine-6-phosphate or a pharmaceutically acceptable salt thereof and a compound of the vitamin A family as combination product for a use which is simultaneous, separate or spread out over time, for the treatment of psoriasis, atopic dermatitis, eczema, joint disorders, disorders related to cartilage deficiency, synovial effusions, for modulation of the inflammatory response, for viscosupplementation, and in treatments associated with surgery, in particular of the eye and abdomen.

Lastly, the present invention relates to a device comprising a pharmaceutical, veterinary or cosmetic composition according to the present invention, preferably a composition comprising N-acetylglucosamine-6-phosphate or a pharmaceutically acceptable salt thereof and a compound of the vitamin A family, the device being suitable for injection (preferably intraepidermal and/or intradermal and/or transdermal and/or subcutaneous and/or micro-injection and/or intra-articular injection) or for topical administration.

BRIEF DESCRIPTION OF DRAWINGS

FIG. 3 presents an analysis of glycosaminoglycan production in skin after treatment with N-acetylglucosamine-6-phosphate.

FIG. 4 presents an analysis of CD44 receptor expression in skin after treatment with N-acetylglucosamine-6-phosphate.

DETAILED DESCRIPTION OF THE INVENTION

Figure 1:
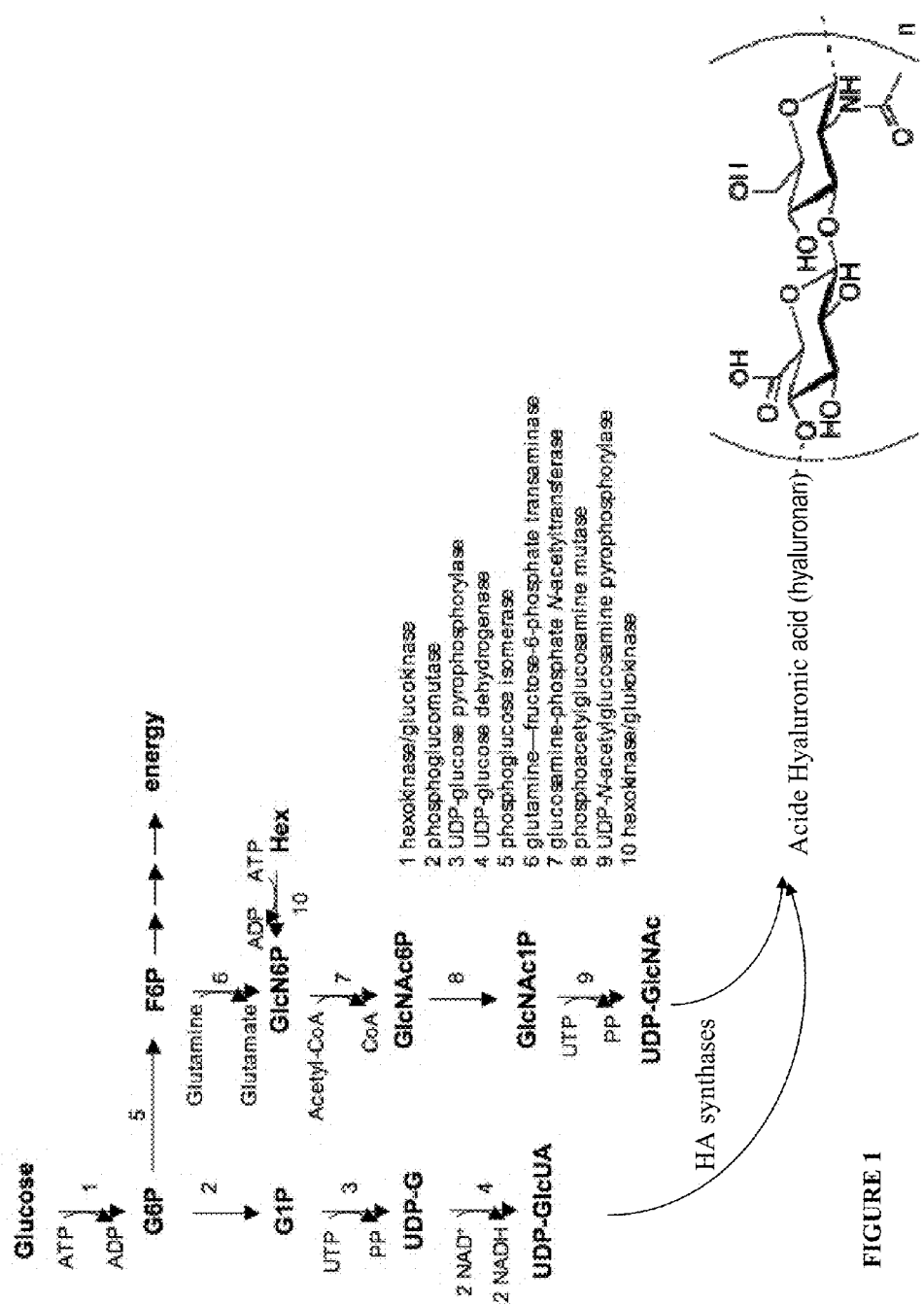
FIG. 1 shows the pathway of hyaluronan synthesis in mammalian cells.

The inventors have, for the first time, tested and identified the effects of N-acetylglucosamine-6-phosphate as exogenous compound (that is to say, obtained by a technical method not involving any component of the human body) on human cells. They have shown in a surprising manner that this chemical entity may be used in pharmaceutical, dermatological, veterinary and cosmetic compositions, alone or in combination with other compounds, in particular those of the vitamin A family, to promote beneficial effects on health and esthetics, through different mechanisms including:

stimulation of the synthesis of structural macromolecules of the human body, including glycosaminoglycans such as hyaluronan and collagens, in particular procollagen 1;

increase in the production of CD44, the hyaluronic acid receptor;

stimulation of cell division, in particular that of keratinocytes and fibroblasts; and, strengthening of the dermal-epidermal junction.

More specifically, the inventors have demonstrated the ability of N-acetylglucosamine-6-phosphate to increase hyaluronan production by keratinocytes or by fibroblasts. They have furthermore demonstrated the ability of N-acetylglucosamine-6-phosphate to stimulate fibroblast cell division. N-acetylglucosamine-6-phosphate also enhances the synthesis of collagen, in particular procollagen 1, by fibroblasts, especially when they are treated with the supernatant of keratinocytes treated with the combination of N-acetylglucosamine-6-phosphate and compounds of the vitamin A family. Finally, in human skin models, the inventors have shown that treatment with N-acetylglucosamine-6-phosphate stimulates glycosaminoglycan synthesis in a way which is well distributed over the entire dermis, stimulates the dermal-epidermal junction and stimulates expression of the CD44 receptor in the dermis and epidermis.

The inventors have further demonstrated the synergistic or potentiating effects of the combination of N-acetylglucosamine-6-phosphate and compounds of the vitamin A family, in particular retinol.

In contrast, N-acetylglucosamine, alone or in combination with a compound of the vitamin A family, has unfavorable effects, or no effects, or effects which are not comparable to those of N-acetylglucosamine-6-phosphate.

Collagen also represents a very large group of structural polymers in the human body. Collagen is the most abundant protein in the body, making up 25-35% of whole-body protein content. It is produced by connective tissue cells. Procollagen 1 in particular is found in tendons, skin, artery walls, the endomysium of striated myofibrils, fibrocartilage and the organic part of bones and teeth. It is a major component of the extracellular matrix of the dermis, playing the role of structural support. Skin aging is due to atrophy of the epidermis, the result of a slowdown in keratinocyte proliferation. It also leads to a decrease in collagen and therefore to a thinning of the dermis, which is aggravated by sun and UV exposure and smoking. Collagen and hyaluronic acid are agents that are known to fight against wrinkles and fine lines.

The dermal-epidermal junction is also crucial for proper nutrition of the epidermis and elasticity of the skin.

This is why N-acetylglucosamine-6-phosphate, optionally in combination with a compound of the vitamin A family, is of great interest in a cosmetic composition intended to prevent or reduce the effects of aging of the skin and appendages, in particular the hair. Such composition is therefore useful to prevent or reduce wrinkles, in particular deep wrinkles and/or fine lines, to improve skin elasticity, to tighten the skin. In an embodiment wherein the composition of the invention is injected (in particular by micro-injection), it can be used for filling wrinkles and fine lines and for enhancing lip volume. In this embodiment, it may additionally comprise or be used in combination with filler products, particularly resorbable products such as hyaluronic acid, fats, collagen or proteins or non-resorbable agents such as polyacrylamide gels or silicones. It may also be used to regenerate or strengthen the dermal-epidermal junction. It may be used to stimulate skin cells (in particular melanocytes, keratinocytes and/or fibroblasts) for example by increasing their proliferation and/or cell migration and/or synthesis of structural macromolecules, in particular collagen and hyaluronan. Such composition therefore makes it possible to maintain and/or strengthen the dermis and/or epidermis, to maintain and/or enhance the thickness thereof, to maintain and/or strengthen the tone and elasticity of the skin. Such composition is appropriate for body and/or facial and/or neck and/or hair care.

In a first particular embodiment, N-acetylglucosamine-6-phosphate may be the only active ingredient or agent of the composition. In a second particular embodiment, N-acetylglucosamine-6-phosphate and the compound of the vitamin A family may be the only active ingredients or agents of the composition. In another particular embodiment, the composition comprises other active ingredients or agents. Examples of these other active ingredients or agents are described below. Active ingredient or agent shall be understood to mean compounds which have a biological effect.

In this application, the cosmetic composition may be formulated to be suitable for administration by the oral route, by the topical route on the skin, scalp or hair, or by intraepidermal and/or intradermal and/or transdermal and/or subcutaneous injection and/or micro-injection.

The cosmetic composition according to the present invention for topical administration may be formulated as aqueous solutions, hydroalcoholic solutions, emulsions [oil in water (O/W), water in oil (W/O) or multiple (for example triple O/W/O or W/O/W)], nanoemulsions, aqueous gels or fatty phase dispersions in an aqueous phase. It may be formulated as a more or less fluid cream, gel, hydrogel, film-forming product (in particular containing high molecular weight hyaluronic acid which has the property of trapping water and forming a gel when spread), lotion, mask, milk, oil, ointment, wax, foam, paste, serum, balm, aerosol, stick, soap or shampoo.

The cosmetic composition suitable for topical administration may be used in combination with mechanical components such as massage-roller devices having a mechanical and rubbing action to facilitate penetration of the product and activating circulation of the product or wave-emitting systems (light, low frequencies, infrared frequencies, etc.) which activate the response of the skin or directly enhance the product's effect.

The cosmetic composition according to the present invention for oral administration may be in the form of a sachet, pill, capsule, syrup or tablet.

The cosmetic composition according to the present invention for injectable delivery is preferably formulated as sterile. It may also be in the form of a powder, the solvent being added immediately before use.

The components of the cosmetic composition and the proportions thereof may be easily chosen by one of skill in the art on the basis of his general knowledge. For example, the composition may include, but is not limited to, deionized water, magnesium, aluminium silicate, xanthan gum, nylon-12, sodium PCA, propylene glycol, red iron oxides, talc, yellow iron oxides, black iron oxides, titanium dioxide, glycerol stearate, stearic acid, DEA-cetyl phosphate, methylparaben, butylparaben, ethylparaben, propylparaben, isopropylparaben, isobutylparaben, isostearyl neopentanoate, isopropyl palmitate, ethylene/propylene/styrene, copolymers, buthylene/propylene/styrene copolymer, phenoxyethanol, tocopheryl acetate, glycerin, triethylamine, stearic acid, propylene glycol stearate, mineral oils, diazolidinyl urea, hydrogenated polyisobutene, octyl palmitate, tridecyl neopentanoate, octyldodecyl neopentanoate, fragrances, octyl methoxycinnamate, benzophenone, octyl salicylate, isopropyl isostearate, isoceteth-3 actetate and combinations thereof.

The cosmetic composition may also be comprised in a device suitable for the desired method of administration.

Such devices may be suitable for topical administration. These include in particular patches, occlusive dressings, occlusive mini-chambers, and the like. Patch shall be understood to mean any type of patch known to one of skill in the art, and in particular those which generate a mild current on the skin when affixed thereto, thereby promoting penetration of the product in the skin. Occlusive mini-chambers shall be understood to mean a small pocket-like device which adheres to the skin, filled with the cosmetic composition and which allows a large amount of said composition to be maintained in contact with the skin in order to increase the amount of product that will diffuse therein.

Other devices will be suitable for injection, in particular for intraepidermal and/or intradermal and/or transdermal and/or subcutaneous injection and/or micro-injection. Such devices may comprise a needle, microneedles or a needle-free injection device. Such devices are well known in mesotherapy. The invention relates to kits comprising the composition according to the present invention and a syringe or an injection device.

A composition comprising N-acetylglucosamine-6-phosphate, optionally in combination with a compound of the vitamin A family, may also be useful for the production of human tissues in vitro or ex vivo, in particular synthetic skin for example in the tissue engineering context. Thus, the present invention relates to a method for producing a human tissue, preferably a cutaneous or connective tissue, comprising contacting cells of the tissue or capable of forming the tissue with a composition comprising N-acetylglucosamine-6-phosphate, optionally in combination with a compound of the vitamin A family. Preferably the cells comprise keratinocytes and/or fibroblasts.

By virtue of the effect of N-acetylglucosamine-6-phosphate, optionally in combination with a compound of the vitamin A family, on the synthesis of glycosaminoglycans, in particular hyaluronan, a pharmaceutical or veterinary composition comprising such active ingredient(s) may be used for the treatment or prevention of joint disorders or those related to cartilage deficiency, for example such as arthritis, arthrosis, osteoarthritis and osteoarthrosis, for stimulation of the synthesis of natural lubricant, for viscosupplementation and/or for the treatment of synovial effusion in humans and animals. In the present application, the animals in question are preferably mammals, for example horses or companion animals such as dogs and cats. The present invention therefore relates to the use of N-acetylglucosamine-6-phosphate, optionally in combination with a compound of the vitamin A family, for preparing a pharmaceutical or veterinary composition intended to treat or prevent joint disorders or those related to cartilage deficiency, for example such as arthritis, arthrosis, osteoarthritis and osteoarthrosis, for stimulation of the synthesis of natural lubricant, for viscosupplementation and/or for the treatment of synovial effusion in humans and animals. Alternatively, the invention also discloses the use of N-acetylglucosamine-6-phosphate for preparing a pharmaceutical or veterinary composition intended for the applications described earlier for a use or administration in combination with a compound of the vitamin A family. The invention also relates to a method for treating joint disorders or those related to cartilage deficiency, for example such as arthritis, arthrosis, osteoarthritis and osteoarthrosis, a method for treating synovial effusion, a method of viscosupplementation or stimulation of the synthesis of natural lubricant, in a human or an animal who so requires, comprising administering an effective amount of N-acetylglucosamine-6-phosphate, optionally in combination with a compound of the vitamin A family. In the applications encompassed in this embodiment, N-acetylglucosamine-6-phosphate, optionally in combination with a compound of the vitamin A family, may be administered or formulated in a form which is suitable for topical or oral administration or injection. Injection may take place for example by the intra-articular, subcutaneous, intramuscular route.

Moreover, in consideration of the beneficial effects of N-acetylglucosamine-6-phosphate on the skin, a pharmaceutical, dermatological or veterinary composition comprising N-acetylglucosamine-6-phosphate, optionally in combination with a compound of the vitamin A family, may be used for the treatment or prevention of psoriasis, eczema, atopic dermatitis or dry skin.

In consideration of the exceptional effect of the combination of N-acetylglucosamine-6-phosphate with a compound of the vitamin A family, notably on hyaluronan production by keratinocytes and fibroblasts, on fibroblast cell division and on collagen production by fibroblasts, the present application more particularly provides a pharmaceutical, dermatological or veterinary composition comprising said combination. This composition is useful for regeneration of damaged tissues. Thus, the present invention relates to the use of N-acetylglucosamine-6-phosphate and a compound of the vitamin A family for preparing a pharmaceutical, dermatological or veterinary composition intended to regenerate damaged tissues and to a method for regenerating damaged tissues in a subject who so requires, comprising administering an effective amount of N-acetylglucosamine-6-phosphate and a compound of the vitamin A family.

In particular, the pharmaceutical, dermatological or veterinary compositions according to the invention may be used in a treatment accompanying or following surgery of the eye (for example cornea transplantation, glaucoma, retinal detachment or cataract), surgical or dermatological procedures on the skin (for example lifting, injection of fillers, peeling, whitening, dermabrasion, acne treatment), surgery of the abdomen. In this embodiment, the pharmaceutical or veterinary compositions combining N-acetylglucosamine-6-phosphate and a compound of the vitamin A family will be preferred.

For all the applications described in the present application, the following wordings shall all be considered interchangeable:

pharmaceutical or veterinary composition comprising N-acetylglucosamine-6-phosphate or a pharmaceutically acceptable salt thereof, optionally in combination with a compound of the vitamin A family, for a use for . . .

use of N-acetylglucosamine-6-phosphate or a pharmaceutically acceptable salt thereof, optionally in combination with a compound of the vitamin A family, for preparing a pharmaceutical or veterinary composition for . . .

product comprising N-acetylglucosamine-6-phosphate or a pharmaceutically acceptable salt thereof and a compound of the vitamin A family as combination product for a use which is simultaneous, separate or spread out over time for . . .

method for . . . in a subject who so requires comprising administering an effective amount of pharmaceutically acceptable N-acetylglucosamine-6-phosphate, optionally in combination with a compound of the vitamin A family.

For all these applications, one embodiment is based on the combined use of N-acetylglucosamine-6-phosphate and a compound of the vitamin A family, in particular retinol, and on a composition comprising such combination.

The pharmaceutical or veterinary composition may be formulated to be suitable for administration by the oral route, by inhalation, by the topical route (in particular on the skin, scalp, eye or a mucous membrane, for example buccal, vaginal or nasal), rectally, or by parenteral, intraepidermal, intradermal, transdermal, subcutaneous, intramuscular, intravenous, intra-articular, intrasynovial, intrasternal, intrathecal, intrahepatic, intralesional, or intracranial injection or by infusion techniques. Preferably, the pharmaceutical or veterinary composition may be formulated to be suitable for administration by the oral route, by inhalation, by the topical route (in particular on the skin, scalp, eye or a mucous membrane, for example buccal, vaginal or nasal), rectally, or by intraepidermal, intradermal, transdermal, subcutaneous, intra-articular or intrasynovial injection. For example, the pharmaceutical or veterinary composition may be formulated in the form of sachets, tablets, capsules, syrups, creams, lotions, gels. The composition may comprise excipients including, but not limited to, talc, lactose, magnesium stearate, glycerol monostearate, colloidal or precipitated silicium dioxide, reticulated polyvinyl pyrrolidone, dibasic calcium phosphate dihydrate, microcrystalline cellulose, starch, povidone, sodium carboxymethyl cellulose, polysorbate 80, lactic acid, carbomer, cetyl alcohol, isopropyl myristate, isopropyl palmitate, glucose, dextrose, triethylamine, glycerin, fructose, sucrose, polymers and nanostructures. The pharmaceutical or veterinary composition may also be comprised in a device suitable for the desired method of administration. The formulations described for the cosmetic composition are applicable to the pharmaceutical or veterinary composition.

In the case of oral formulations, and in particular tablets, the carrier often comprises lactose and starch. Lubricating agents such as magnesium stearate are also added. In the case of capsules, diluents include lactose and starch. For aqueous suspensions, the active ingredient is combined with emulsifiers and suspending agents. It is also possible to incorporate sweeteners, colorants and flavorings.

In the case of rectal formulations, such as suppositories, these formulations may be prepared by mixing the active ingredient with suitable excipients which are solid at room temperature but fluid at rectal temperature. Such materials include cocoa butter, beeswax and polyethylene glycols.

For topical administration, the composition may be formulated in particular in the form of an ointment containing the active ingredient dissolved or suspended in appropriate carriers. Such carriers include but are not limited to mineral oils, liquid vaseline, white vaseline, propylene glycol, polyoxyethylene, polyoxypropylene, emulsifier wax and water. Alternatively, it may be formulated as a cream or lotion containing the active ingredient dissolved or suspended in appropriate carriers. Such carriers include but are not limited to mineral oils, sorbitan monostearate, polysorbate 60, cetyl ester wax, cetearyl alcohol, 2-octyldodecanol, benzyl alcohol and water.

For an ophthalmic application, the composition may be formulated as a micronized suspension in sterile isotonic saline solution at adjusted pH or preferably as a solution in sterile isotonic saline solution at adjusted pH, with or without an antimicrobial preservative such as benzalkonium chloride. Alternatively, the composition may also be formulated as an ointment containing a material such as vaseline.

In injectable forms the composition may be an aqueous or oleaginous suspension. Such suspensions may be formulated by methods well known to one of skill in the art by using wetting agents or dispersants and suspending agents. Preferably, the composition will be a sterile solution or suspension. Acceptable solvents and carriers include but are not limited to water, Ringer's solution and isotonic sodium chloride. In addition, sterile fixed oils are often used in the suspension medium or solvent. To this end, any mixed fixed oil may be used, such as mono- and diglycerides. Fatty acids like oleic acid and its glyceride derivatives are also used for preparing injectable compositions, as are pharmaceutically acceptable natural oils like olive oil, castor oil, in particular their polyoxyethylenated forms. These oily solutions may comprise suspending agents or diluents like carboxymethyl cellulose for the formulation of emulsions and suspensions. Surfactants like the Tweens, emulsifiers, agents that increase bioavailability may also be included.

N-acetylglucosamine-6-phosphate is a compound that is not available in large amounts. Therefore, it is preferably prepared by the method described in patent application WO08/142,155 (in particular in example 1), the content of which is incorporated by reference in the present application. In particular, N-acetylglucosamine of marine origin (derived from shrimp or crab chitin) is mixed with the selected inorganic phosphate and the suitable phosphorylating enzyme in a reactor containing water and salts for several hours. During this reaction, the enzyme adds a phosphate group to N-acetylglucosamine to produce N-acetylglucosamine-6-phosphate. This compound can then be purified with the aid of several precipitation steps using different alcohols (such as isopropanol and/or ethanol). The final aqueous solution is purified on an ion exchange resin to remove remaining ions. N-acetylglucosamine-6-phosphate can be concentrated in water and sterilized by microfiltration (0.2 µm filter). The final purity can be evaluated by analytical methods. This method permits the preparation of N-acetylglucosamine-6-phosphate that can be used directly from the concentrated aqueous solution or that can be dried to obtain a crystalline powder that dissolves rapidly in any aqueous formula.

N-acetylglucosamine-6-phosphate may also be used in the compositions and products of the invention in the form of salts, in particular a pharmaceutically or cosmetically acceptable salt. For instance, such salts include in particular acid addition salts, basic addition salts, metal salts, and ammonium or alkyl ammonium salts, in particular those which are pharmaceutically or cosmetically acceptable. Acid addition salts include inorganic salts and organic salts. Representative examples of appropriate inorganic acids comprise hydrochloric, hydrobromic, iodic, phosphoric acids and the like. Representative examples of appropriate organic acids comprise acetic, formic, propionic, benzoic, maleic, fumaric, succinic, tartaric, citric, trichloroacetic, trifluoroacetic acids and the like. Other examples of organic or inorganic acid addition salts are given in J. Pharm Sci., 1977, 66, 2 and in the "Handbook of Pharmaceutical Salts: Properties, Selection and Use", P. Heinrich Stahl and Camille G. Wermuth, eds., 2002. Examples of metal salts include lithium, sodium, potassium or magnesium salts and the like. Examples of ammonium or alkyl ammonium salts include ammonium, methyl-ammonium, dimethyl-ammonium, trimethyl-ammonium, ethyl-ammonium, hydroxyethyl-ammonium, diethyl-ammonium, butyl-ammonium, tetramethyl-ammonium salts and the like. Examples of organic bases include lysine, arginine, guanidine, diethanolamine and the like.

The compositions of the present invention, whether cosmetic, pharmaceutical, dermatological or veterinary, may comprise a physiologically acceptable carrier, preferably acceptable in the cosmetic, pharmaceutical, dermatological or veterinary fields, respectively.

In the spirit of the present application, "compound of the vitamin A family" shall be understood to mean a compound selected from the group consisting of retinol (also known as vitamin A), retinal or retinaldehyde (cis or trans), retinoic acid (trans), retinaldehyde, isotretinoin (cis-retinoic acid), adapalene, tretinoin (trans-retinoic acid), the salts and derivatives thereof and the mixture thereof. Preferably, the compound is selected from the group consisting of retinol, retinal and retinaldehyde (cis or trans), retinoic acid, retinaldehyde, isotretinoin, tretinoin, the salts and derivatives thereof and the mixture thereof. Vitamin A derivatives may be a vitamin A ester (for example vitamin A acetate, vitamin A propionate, or vitamin A palmitate), a vitamin A phosphate, or a pro-vitamin A (for example, β-carotene). In a particular embodiment, the compound of the vitamin A family is retinol or a salt or an alcohol or an ester thereof.

The amount of N-acetylglucosamine-6-phosphate used in the compositions and products of the invention depends on the cosmetic or therapeutic effect and may therefore vary. In a particular embodiment, a range of N-acetylglucosamine-6-phosphate concentrations comprised between approximately 0.001 g/L or g/kg and approximately 1000 g/L or g/kg of composition, and preferably comprised between approximately 0.01 g/L or g/kg and approximately 100 g/L or g/kg, and more preferably comprised between approximately 0.1 g/L or g/kg and approximately 10 g/L or g/kg of composition, appears appropriate, more particularly for topical administration.

In a more preferred embodiment, the compound of the vitamin A family is combined with N-acetylglucosamine-6-phosphate in a synergistic or potentiating amount.

In a particular embodiment, the compound of the vitamin A family, in particular retinol, an ester or a salt thereof, is present in the composition at a concentration comprised between approximately 3 µg/L or µg/kg and approximately 3 g/L or g/kg of composition and preferably between approximately 100 mg/L or mg/kg and approximately 1.5 g/L or g/kg of composition.

One of the drawbacks of retinol is that it causes undesirable side effects, and in particular skin irritation. Synergy or the potentiating effect has been demonstrated at low concentrations, in particular at concentrations lower than those generally used in cosmetics and therapy. Thus, in a preferred embodiment, the compound of the vitamin A family is combined with N-acetylglucosamine-6-phosphate in an amount which is non- or less toxic and non- or less irritant in accordance with the final use of the composition. Thus, in this particular embodiment, the compound of the vitamin A family, in particular retinol, an ester or a salt thereof, is present in the composition at a concentration comprised between approximately 3 µg/L or µg/kg and approximately 50 mg/L or mg/kg of composition and preferably between approximately 3 µg/L or µg/kg and approximately 10 mg/L or mg/kg of composition.

The compositions and kits of the present invention may additionally comprise other components, in particular compounds having an effect. In particular, they may comprise for example free radical scavengers, preferably stabilized polyphenols such as those described in patent application US 2009/0233876. Furthermore, they may also comprise phosphatase inhibitors to avoid degradation of N-acetylglucosamine-6-phosphate to N-acetylglucosamine, for example cysteine. They may also comprise hyaluronidase inhibitors to prevent or decrease the degradation of newly synthesized hyaluronan produced under the stimulation of N-acetylglucosamine-6-phosphate, for example 6-palmitoyl-L-ascorbic acid, ascorbic acid 6-hexadecanoate. They may comprise activators of hyaluronan synthases so as to accelerate the synthesis of hyaluronan stimulated by N-acetylglucosamine-6-phosphate and have a synergistic action therewith, for example eicosanoids such as prostaglandin E2, or retinoic acids (trans). They may comprise glucuronic acid derivatives, such as for example glucuronic acid, its salts, esters and amides or UDP-glucuronic acid, in order to accelerate the synthesis of hyaluronan stimulated by N-acetylglucosamine-6-phosphate and have a synergistic action with the latter.

The invention will become clearer in the following examples which are given for purposes of illustration by describing only certain embodiments and certain advantageous properties of the invention, and not by way of limitation.

EXAMPLES

Example 1: Stimulation of Hyaluronic Acid Production by Human Keratinocytes Treated with N-Acetylglucosamine-6-Phosphate 1. Principle of the Test Normal human keratinocytes were cultured to confluence. Cells were treated with the test products for 48 hours. The supernatants, containing hyaluronic acid, were collected and assayed immediately. Hyaluronic acid was quantified with an ELISA microtiter plate.

Protein content was determined for each well of the microtiter plate.

2. Product Tested

N-acetylglucosamine-6-phosphate (NAG6P) was tested at concentrations of 20, 10 and 5 mM.

3. Preparation of Cells

Primocultures of normal human keratinocytes (NHK) were obtained from cells isolated from skin specimens from plastic surgery.

NHK were seeded at a density of 130,000 cells/well in specific KSFM culture medium (Gibco®, Invitrogen) in a 24-well plate. The plate was placed in a humid incubator (37° C., 5% $CO_2$) for 24 hours.

4. Treatment of Cells

The different products at the respective concentrations (diluted in KSFM medium, 600 µl) were contacted with the cells for 48 hours. Untreated cells were used as the control condition.

Each treatment condition was evaluated on three wells of NHK cells.

5. Hyaluronic Acid Assay

After 24 hours of treatment, an intermediate sample of 220 µA of supernatant was removed from each well and the plate returned to the incubator (37° C., 5% $CO_2$).

After 48 hours of treatment, the remaining supernatant (≈350 µA) was collected and centrifuged.

Cell supernatants were assayed according to the method described in the Hyaluronan Enzyme-Linked Immunosorbent Assay kit (HA-ELISA, Echelon Biosciences Inc.). This is an ELISA assay with spectrophotometric detection at 405 nm (Safire, Tecan).

The assay was performed in duplicate for each well.

6. Expression of Results

Optical densities (OD) measured on each sample were plotted on a graph (specific standard curve in the kit). The hyaluronic acid concentration was expressed in ng/ml.

7. Protein Synthesis

This involved determining the protein content in the cell pellets of the supernatants for which hyaluronic acid was assayed.

The results were expressed as µg of protein per well.

The bicinchoninic acid (BCA) method was used, which is similar in principle to the Lowry method.

7.1. Principle

Proteins reduce $Cu^{++}$ to $Cu^+$ in a dose-dependent manner. Bicinchoninic acid is a chromogen highly specific for $Cu^+$ ions with which it forms a colored complex whose absorbance is measured at 550 nm.

7.2. Reagents

Two solutions were used in the assay: bicinchoninic acid and copper sulfate. When these two reagents are mixed, they form a green solution which is reduced to purple in the presence of $Cu^+$ ions.

These reagents are supplied in the BCA-1 assay kit from Sigma. A standard protein solution (BSA 1 mg/ml in 0.15 M NaCl) is also supplied.

7.3. Protein Assay

After 48 hours of treatment, supernatants from the microtiter wells were removed to assay hyaluronic acid. The cell layer was then taken up in PBS, detached by sonication and dissolved in 0.1M NaOH. The bicinchoninic acid+copper sulfate mixture was then added and the plate placed in a humid incubator (37° C., 5% $CO_2$) in the dark. After a 30 minute incubation, absorbance was measured at 550 nm (Genios, Tecan).

In parallel, a standard curve was prepared using BSA 1 mg/ml stock solution (P-0914) over a concentration range of 0 to 100 μg/well.

This standard curve was used to convert optical densities measured on the wells to μg of protein per well of NHK cells.

7.4. Expression of Results

The amount of hyaluronic acid released by the cells was determined for each well and for each treatment condition, relative to the cell content expressed as μg of protein. Thus, the final result was expressed as ng/ml of hyaluronic acid per μg of protein.

A mean value was calculated for wells treated with the same concentration of test product. This mean was compared with the mean of the control wells (Student t test–comparison of means–significant difference at 95% if $p<0.05$* and at 99% if $p<0.01$*).

The percent stimulation induced by the test products was determined by comparing the mean values of the control and treatment conditions:

% Stimulation=(Treated−Control)/Control

The results are shown in Tables 1 and 2 (abbreviation: NAG6P: N-acetylglucosamine-6-phosphate).

TABLE 1

Hyaluronic acid produced by the keratinocytes after 24 hours

| 24 hrs - NAG6P | Hyaluronic acid (ng/ml) | % stimulation of hyaluronic acid synthesis |
|---|---|---|
| Control | 789.5 ± 229 | |
| NAG6P 10 mM | 1067.3 ± 111.9 | 35%* |

*Student test: p < 0.05 - result significant at 95%

TABLE 2

Hyaluronic acid produced by the keratinocytes after 48 hours

| 48 hrs - NAG6P | Hyaluronic acid (ng/ml) | Protein (μg/well) | (ng/ml/μg prot.) | % stimulation of hyaluronic acid synthesis |
|---|---|---|---|---|
| Control | 1243.4 ± 232.3 | 17.9 ± 1.4 | 70.5 ± 18.4 | |
| NAG6P 20 mM | 3076 ± 260.8 | 11.7 ± 1.9 | 269.6 ± 55.3 | 282%** |
| NAG6P 10 mM | 2503.2 ± 552.8 | 15.3 ± 2.9 | 165.7 ± 32.4 | 135%** |
| NAG6P 5 mM | 1817.9 ± 145.1 | 15.2 ± 2 | 122.1 ± 25.6 | 73%* |

*Student test: p < 0.05 - result significant at 95%
**Student test: p < 0.01 - result significant at 99%

Conclusions:

Addition of N-acetylglucosamine-6-phosphate to normal human keratinocytes stimulated hyaluronic acid production by these skin cells in a dose-dependent manner, after 24 hours of treatment. At 48 hours the stimulation was confirmed and further enhanced with a +282% increase in hyaluronic acid production as compared to cells not treated with N-acetylglucosamine-6-phosphate.

N-acetylglucosamine-6-phosphate is therefore an excellent stimulator of hyaluronic acid production by skin cells. NAG6P is therefore of interest for stimulating the renewal of the epidermal extracellular matrix of the skin, so as to limit the formation of wrinkles and fine lines, or promote their attenuation, and to promote and maintain hydration of the skin (thanks to the high water-holding capacity of hyaluronic acid).

Example 2: Stimulation of Hyaluronic Acid Production by Human Keratinocytes Treated with N-Acetylglucosamine-6-Phosphate in Synergy with Vitamin A Propionate A study was carried out under the conditions described in example 1, using vitamin A propionate in combination with N-acetylglucosamine-6-phosphate. The vitamin A propionate was dissolved in DMSO.

For this test of vitamin A propionate+/−NAG6P, the percent stimulation was expressed relative to the DMSO control (1:10,000 dilution corresponding to the amount of DMSO actually present) in place of the Control.

The results are shown in Tables 3 and 4 (abbreviation: NAG6P: N-acetylglucosamine-6-phosphate).

TABLE 3

Hyaluronic acid produced by the keratinocytes after 24 hours

| 24 hrs - Synergy | Hyaluronic acid (ng/ml) | % stimulation of hyaluronic acid synthesis |
|---|---|---|
| Control | 789.5 ± 229 | |
| NAG6P 10 mM | 1067.3 ± 111.9 | 35%* |
| Vit. A propionate 1 μM | 1056 ± 186.5 | 34%* |
| NAG6P 10 mM + Vit. A propionate 1 μM | 1569.6 ± 193 | 99%** |

*Student test: p < 0.05 - result significant at 95%
**Student test: p < 0.01 - result significant at 99%

TABLE 4

Hyaluronic acid produced by the keratinocytes after 48 hours

| 48 hrs - Synergy | Hyaluronic acid (ng/ml) | Protein (μg/well) | (ng/ml/μg prot.) | % stimulation of hyaluronic acid synthesis |
|---|---|---|---|---|
| Control | 1243.4 ± 232.3 | 17.9 ± 1.4 | 70.5 ± 18.4 | / |
| NAG6P 10 mM | 2503.2 ± 552.8 | 15.3 ± 2.9 | 165.7 ± 32.4 | 135%** |
| DMSO control[a] | 1028.9 ± 122.8 | 15.6 ± 3.3 | 66.9 ± 7.7 | / |
| Vit. A propionate 1 μM | 1944.8 ± 393.2 | 14.3 ± 1 | 137.1 ± 32.2 | 105%* |
| NAG6P 10 mM + Vit. A propionate 1 μM | 3833.3 ± 216.3 | 13.5 ± 2 | 287.4 ± 35.7 | 330%** |

[a]DMSO control: 1:10,000 dilution corresponding to amount of DMSO present in the treatment with vitamin A propionate and the combination NAG 10 mM + Vit. A propionate 1 μM.
*test Student: p < 0.05 - result significant at 95%
**test Student: p < 0.01 - result significant at 99%

Conclusions:

In a remarkable manner, it was observed that by combining N-acetylglucosamine-6-phosphate with vitamin A propionate, a synergistic stimulation of hyaluronic acid production by keratinocytes occurred starting from 24 hours. Even more remarkably, said effect was greater than the sum of the effects of each compound tested separately (+99% increase in hyaluronic acid levels at 24 hours with both compounds versus +34% and +35%, respectively, with vitamin A propionate alone and N-acetylglucosamine-6-phosphate alone).

This synergistic effect was confirmed and enhanced after 48 hours, at which time the combination of N-acetylglucosamine-6-phosphate and vitamin A propionate induced a +330% increase in hyaluronic acid production by keratinocytes, versus +105% and +135%, respectively, with vitamin A propionate alone and N-acetylglucosamine-6-phosphate alone.

The combination of N-acetylglucosamine-6-phosphate with a vitamin A derivative therefore improves the effectiveness of N-acetylglucosamine-6-phosphate on stimulating hyaluronic acid production by skin cells. NAG6P acting synergistically with vitamin A propionate is therefore of interest for stimulating the renewal of the epidermal extracellular matrix of the skin, so as to limit the formation of wrinkles and fine lines, or promote their attenuation, and to promote and maintain hydration of the skin (thanks to the high water-holding capacity of hyaluronic acid).

Example 3: Indirect Stimulation (Mediated by Keratinocytes) of Hyaluronic Acid Production by Normal Human Fibroblasts Via N-Acetylglucosamine-6-Phosphate Alone or in Combination with Vitamin A Propionate—Comparison with N-Acetylglucosamine 1. Principle of the Test Normal human dermal fibroblasts were cultured to confluence. Cells were treated for 48 hours with supernatants of normal human keratinocytes previously grown in the presence of the test products. The fibroblast supernatants, containing hyaluronic acid, were collected and assayed immediately. Hyaluronic acid was quantified with an ELISA microtiter plate. Protein content was determined for each well of the microtiter plate.

2. Products Tested

N-acetylglucosamine (NAG) or N-acetylglucosamine-6-phosphate (NAG6P) at 10 or 5 mM concentration was applied for 48 hours on normal human keratinocytes, after which the supernatant was transferred to normal human fibroblasts.

Vitamin A propionate 1 µM was applied for 48 hours on normal human keratinocytes, after which the supernatant was transferred to normal human fibroblasts.

The combination of NAG 10 mM+Vitamin A propionate 1 µM was applied for 48 hours on normal human keratinocytes, after which the supernatant was transferred to normal human fibroblasts.

The combination of NAG6P 10 mM+Vitamin A propionate 1 µM was applied for 48 hours on normal human keratinocytes, after which the supernatant was transferred to normal human fibroblasts.

3. Preparation of Cells

Primocultures of normal human keratinocytes (NHK) were obtained from cells isolated from skin specimens from plastic surgery.

NHK were seeded at a density of 130,000 cells/well in specific KSFM culture medium (Gibco®, Invitrogen) in a 24-well plate. The plate was placed in a humid incubator (37° C., 5% $CO_2$) for 24 hours.

Primocultures of normal human fibroblasts (NHF) were obtained from cells isolated from skin specimens from plastic surgery.

NHF were seeded at a density of 90,000 cells/well in E-199 culture medium supplemented with 0.5% FCS (Gibco® Invitrogen) in a 24-well plate. The plate was placed in a humid incubator (37° C., 5% $CO_2$) for 24 hours.

The two cell types—NHK and NHF—were plated 48 hours apart.

4. Treatment of Cells

The different products at the respective concentrations (diluted in KSFM medium, 600 µl) were contacted with NHK cells for 48 hours. Untreated cells were used as the control condition. Two plates were used to separately test NAG, and NAG+vitamin A propionate, on the one hand, and NAG6P, and NAG6P+vitamin A propionate, on the other hand.

Each treatment condition was evaluated on three wells of NHK cells.

After 48 hours, a fraction of NHK cell supernatant (300 µl/well) was removed and transferred well for well into NHF cell supernatants (300 µl E-199/well–fresh medium without FCS).

This gave a final volume of 600 µl/well (50:50 ratio of KSFM/E-199 medium) which remained on the NHF cells for 48 hours.

5. Hyaluronic Acid Assay

After 48 hours of treatment, the NHF cell supernatant was collected and centrifuged.

Hyaluronic acid was assayed in the cell supernatants as described in example 1.

The assay was performed in duplicate for each well.

6. Expression of Results

Optical densities (OD) measured on each sample were plotted on a graph (specific standard curve in the kit). The hyaluronic acid concentration was expressed in ng/ml.

7. Protein Synthesis

This involved determining the protein content in the cell pellets of the supernatants for which hyaluronic acid was assayed.

The assay was carried out as described in example 1 and the results were expressed as µg of protein per well.

The amount of hyaluronic acid released by the cells was determined for each well and for each treatment condition, relative to the cell content expressed as µg of protein. Thus, the final result was expressed as ng/ml of hyaluronic acid per µg of protein.

A mean value was calculated for wells treated with the same concentration of test product. This mean was compared with the mean of the control wells (Student t test–comparison of means–significant difference at 95% if $p<0.05*$ and at 99% if $p<0.01**$).

The percent stimulation induced by the test products was determined by comparing the mean values of the control and treatment conditions:

% Stimulation=(Treated−Control)/Control

For the conditions of vitamin A propionate+/−NAG or NAG6P (transferred), the percent stimulation was expressed relative to the DMSO control (1:10,000 dilution corresponding to the amount of DMSO actually present) in place of the Control.

The results are shown in Tables 5 and 6 and correspond to the mean of three wells.

TABLE 5

Hyaluronic acid produced by the fibroblasts after 48 hours - effect of NAG alone or in combination with vitamin A propionate

| 48 hrs - NAG | Hyaluronic acid (ng/ml) | Protein (µg/well) | (ng/ml/µg prot.) | % stimulation of hyaluronic acid synthesis |
|---|---|---|---|---|
| Control | 3559.3 ± 374 | 8.4 ± 0.8 | 429.9 ± 78.4 | / |
| NAG 10 mM | 4056.1 ± 315.5 | 15.7 ± 0.6 | 258.8 ± 8.1 | −40%** |
| NAG 5 mM | 4277.6 ± 488 | 12.2 ± 2.7 | 358.9 ± 81.8 | −17% |
| DMSO control[a] | 3001.7 ± 354.6 | 8 ± 2.3 | 387.3 ± 73.4 | / |
| Vit. A propionate 1 µM | 3645.6 ± 667.8 | 12 ± 3.7 | 316.6 ± 68 | −18% |
| NAG 10 mM + Vit. A propionate 1 µM | 4439.4 ± 445.9 | 10 ± 1.2 | 443.4 ± 15.2 | 15% |

[a]DMSO control: 1:10,000 dilution corresponding to amount of DMSO present in the treatment with vitamin A propionate and the combination NAG 10 mM + Vit. A propionate 1 µM.
*Student test: p < 0.05 - result significant at 95%
**Student test: p < 0.01 - result significant at 99%

TABLE 6

Hyaluronic acid produced by the fibroblasts after 48 hours - effect of NAG6P alone or in combination with vitamin A propionate

| 48 hrs - NAG6P | Hyaluronic acid (ng/ml) | Protein (µg/well) | (ng/ml/µg prot.) | % stimulation of hyaluronic acid synthesis |
|---|---|---|---|---|
| Control | 3351 ± 287.4 | 8.9 ± 0.9 | 375.9 ± 13.5 | / |
| NAG6P 10 mM | 3507.6 ± 213.3 | 9.2 ± 0.3 | 382.9 ± 20.5 | 2% |
| NAG6P 5 mM | 3524.1 ± 198.6 | 8.8 ± 0.5 | 401.7 ± 38.3 | 7% |
| DMSO control[a] | 3058 ± 552 | 8.4 ± 0.7 | 364.3 ± 54.2 | / |
| Vit. A propionate 1 µM | 3358.8 ± 615.3 | 8.8 ± 0.9 | 389.2 ± 108.3 | 7% |
| NAG6P 10 mM + Vit. A propionate 1 µM | 4075.4 ± 433.4 | 7.9 ± 0.2 | 517.6 ± 28.2 | 42%** |

[a]DMSO control: 1:10,000 dilution corresponding to amount of DMSO present in the treatment with vitamin A propionate and the combination NAG6P 10 mM + Vit. A propionate 1 µM.
*Student test: p < 0.05 - result significant at 95%
**Student test: p < 0.01 - result significant at 99%

Conclusions:

After incubating keratinocytes for 48 hours in the presence of NAG alone or vitamin A propionate alone, then transferring the cell supernatant onto fibroblasts, a decrease in hyaluronic acid synthesis by these fibroblasts was observed (this decrease was significant with 10 mM NAG). The same experiment carried out with the combination of NAG and vitamin A propionate led to a weak 15% stimulation of hyaluronic acid production by fibroblasts treated with the keratinocyte culture supernatant.

In a surprising manner, by incubating in the same conditions the keratinocytes with NAG6P alone or with vitamin A propionate alone, then transferring the supernatant of these cells onto fibroblasts, a small stimulation of hyaluronic acid production by these fibroblasts was seen. The same experiment carried out with the combination of NAG6P and vitamin A propionate produced a large 42% increase in hyaluronic acid production by fibroblasts treated with the keratinocyte culture supernatant.

Unlike N-acetylglucosamine which had no effect, N-acetylglucosamine-6-phosphate in combination with vitamin A propionate was able to stimulate hyaluronic acid production by dermal cells through the intermediary of keratinocytes. The combination of N-acetylglucosamine-6-phosphate and vitamin A propionate therefore stimulates hyaluronic acid production in cells naturally located in the dermis.

NAG6P acting synergistically with vitamin A propionate is therefore of interest for stimulating the renewal of the dermal extracellular matrix of the skin, so as to limit the formation of wrinkles and fine lines, or promote their attenuation, and to promote and maintain hydration deep in the skin (thanks to the high water-holding capacity of hyaluronic acid).

Example 4: Indirect Stimulation (Mediated by Keratinocytes) of Procollagen 1 Production by Normal Human Fibroblasts Humans Via N-Acetylglucosamine-6-Phosphate Alone or in Combination with Vitamin A Propionate—Comparison with N-Acetylglucosamine 1. Principle This experiment was carried out according to the method described in example 3. Fibroblast supernatants, containing procollagen 1, were collected and assayed immediately for procollagen 1 by means of an EIA microtiter plate.

2. Procollagen 1 Assay

After 48 hours of treatment, NHF cell supernatants were collected and centrifuged.

Procollagen 1 was assayed in the cell supernatants by the method described in the Procollagen Type 1 C-peptide EIA kit (MK101, Takara). This is an EIA assay with spectrophotometric detection at 450 nm (Safire, Tecan).

Duplicate determinations were carried out for two wells whereas the third well was assayed only once.

3. Expression of Results

Optical densities (OD) measured on each sample were plotted on a graph (specific standard curve in the kit). The procollagen 1 concentration was expressed in ng/ml.

As in example 3, the protein content was determined in the cell pellets of the supernatants for which procollagen 1 was assayed.

Thus, the final result was expressed as ng/ml of procollagen 1 per µg of protein. A mean value was calculated for wells treated with the same concentration of test product. This mean was compared with the mean of the control wells (Student t test–comparison of means, significant difference at 95% if p<0.05* and at 99% if p<0.01**).

The percent stimulation produced by the test products was determined by comparing the mean values of the control and treatment conditions:

% Stimulation=(Treated−Control)/Control

For the conditions of vitamin A propionate+/−NAG or NAG6P (transferred), the percent stimulation was expressed relative to the DMSO control (1:10,000 dilution corresponding to the amount of DMSO actually present) in place of the Control.

The results are shown in Tables 7 and 8 and correspond to the mean of three wells.

TABLE 7

Procollagen 1 produced by the fibroblasts after 48 hours - effect of NAG alone or in combination with vitamin A propionate

| 48 hrs - NAG | Procollagen 1 (ng/ml) | Protein (μg/well) | (ng/ml/μg prot.) | % stimulation |
|---|---|---|---|---|
| Control | 767.4 ± 94.3 | 8.4 ± 0.8 | 91.4 ± 20.6 | / |
| NAG 10 mM | 700.9 ± 32.7 | 15.7 ± 0.6 | 44.9 ± 1.3 | −51%** |
| NAG 5 mM | 685.9 ± 38.6 | 12.2 ± 2.7 | 57.3 ± 10.5 | −37%* |
| DMSO control[a] | 611.7 ± 78.7 | 8 ± 2.3 | 75.7 ± 13.7 | / |
| Vit. A propionate 1 μM | 706.1 ± 73.8 | 12 ± 3.7 | 64.3 ± 20.1 | 15% |
| NAG 10 mM + Vit. A propionate 1 μM | 715 ± 26.3 | 10 ± 1.2 | 72.4 ± 9.6 | −4% |

[a]DMSO control: 1:10,000 dilution corresponding to amount of DMSO present in the treatment with vitamin A propionate and the combination NAG 10 mM + Vit. A propionate 1 μM
*Student test: p < 0.05 - result significant at 95%
**Student test: p < 0.01 - result significant at 99%

TABLE 8

Procollagen 1 produced by the fibroblast after 48 hours - effect of NAG6P alone or in combination with vitamin A propionate

| 48 hours - NAG6P | Procollagen 1 (ng/ml) | Protein (μg/well) | (ng/ml/ μg prot.) | % stimulation |
|---|---|---|---|---|
| Control | 675.5 ± 81.8 | 8.9 ± 0.9 | 73.2 ± 4.4 | / |
| NAG6P 10 mM | 677.7 ± 64.6 | 9.2 ± 0.3 | 72.7 ± 4.4 | −1% |
| NAG6P 5 mM | 653.4 ± 36.6 | 8.8 ± 0.5 | 74.6 ± 5.3 | 2% |
| DMSO control[a] | 672.4 ± 67.5 | 8.4 ± 0.7 | 78.0 ± 2.0 | / |
| Vit. A propionate 1 μM | 704.4 ± 38.6 | 8.8 ± 0.9 | 81.9 ± 13.0 | 5% |
| NAG6P 10 mM + Vit. A propionate 1 μM | 744.7 ± 74.9 | 7.9 ± 0.2 | 94.7 ± 3.5 | 21%** |

[a]DMSO control: 1:10,000 dilution corresponding to amount of DMSO present in the treatment with vitamin A propionate and the combination NAG 10 mM + Vit. A propionate 1 μM.
*test Student: p < 0.05 - result significant at 95%
**test Student: p < 0.01 - result significant at 99%

Conclusions:

After incubating keratinocytes for 48 hours in the presence of NAG alone or vitamin A propionate alone, then transferring the cell supernatant onto fibroblasts, a decrease in procollagen 1 synthesis by these fibroblasts was observed (this decrease was significant with 10 mM NAG). The same experiment carried out with the combination of NAG and vitamin A propionate appeared to cause a decrease in procollagen 1 production by these fibroblasts.

In a surprising manner, by incubating in the same conditions the keratinocytes with NAG6P in combination with vitamin A propionate, then transferring the supernatant of these cells onto fibroblasts, a stimulation of procollagen 1 synthesis by these fibroblasts was seen. This stimulation effect obtained by combining NAG6P with vitamin A propionate was greater than the sum of the effects of each compound tested separately.

Unlike N-acetylglucosamine which had no effect, N-acetylglucosamine-6-phosphate in combination with vitamin A propionate was able to stimulate procollagen 1 production by dermal cells through the intermediary of keratinocytes. The combination of N-acetylglucosamine-6-phosphate and vitamin A propionate therefore stimulates procollagen 1 production in cells naturally present in the dermis.

NAG6P is therefore able to induce procollagen 1 production by fibroblasts, via keratinocytes, in synergy with vitamin A propionate, and this combination is therefore of interest for stimulating the renewal of the extracellular matrix of the skin, so as to limit the formation of wrinkles and fine lines, or promote their attenuation, and to promote and maintain hydration deep in the skin (thanks to the high water-holding capacity of hyaluronic acid).

Example 5: Indirect Stimulation (Mediated by Keratinocytes) of Normal Human Fibroblasts Proliferation Via N-Acetylglucosamine Alone or in Combination with Vitamin A Propionate This experiment evaluated the proliferation of normal human fibroblasts (dermal primocultures) after 48 hours of treatment with supernatant transferred from human keratinocytes.

The "Cell Proliferation ELISA, BrdU" test quantifies cell proliferation by measuring incorporation of bromodeoxyuridine (BrdU) during DNA synthesis followed by luminescence detection. This is a sensitive method that does not use radioactivity (an alternative to [$H^3$] thymidine incorporation).

1. Principle

Cells were placed in the presence of the treatment for a specified time (incubator at 37° C., 5% $CO_2$). The pyrimidine analogue 5-bromo-2'-deoxyuridine (BrdU) was then added and the cells were further incubated (37° C., 5% $CO_2$) for a minimum of 2 hours, during which time BrdU is incorporated in place of thymidine into the DNA of proliferating cells.

The culture medium was removed, then the cells were fixed and the DNA denatured at the same time (antibody accessibility). An anti-BrdU-POD (peroxidase) antibody was added; this antibody binds to BrdU in newly synthesized DNA. The immune complex was then detected by addition of luminol substrate with measurement of luminescence (Genios, Tecan).

2. Test Products

N-acetylglucosamine-6-phosphate (NAG6P) was applied at a concentration of 10 and 5 ù % for 48 hours on normal human keratinocytes, after which the supernatant was transferred to normal human fibroblasts.

Vitamin A propionate was applied at 1 μM concentration for 48 hours on normal human keratinocytes, after which the supernatant was transferred to normal human fibroblasts.

The combination NAG6P 10 mM+Vitamin A propionate 1 μM was applied for 48 hours on normal human keratinocytes, after which the supernatant was transferred to normal human fibroblasts.

3. Preparation of Cells

Primocultures of normal human keratinocytes (NHK) were obtained from cells isolated from skin specimens from plastic surgery.

NHK were seeded at a density of 130,000 cells/well in specific KSFM culture medium (Gibco®, Invitrogen) in a 24-well plate. The plate was placed in a humid incubator (37° C., 5% $CO_2$) for 24 hours.

Primocultures of normal human fibroblasts (NHF) were obtained from cells isolated from skin specimens from plastic surgery.

NHF were seeded at a density of 5,000 cells/well in E-199 culture medium (Gibco® Invitrogen) in a 96-well Optilux white plate (BD Falcon 353947). The plate was placed in a humid incubator (37° C., 5% $CO_2$) for 24 hours.

The two cell types—NHK and NHF—were plated 48 hours apart.

4. Treatment of Cells

The different products at the respective concentrations (diluted in KSFM culture medium, 600 µl) were contacted with NHK cells for 48 hours. Control cells were left untreated. Each treatment conditions was evaluated on three wells of NHK cells.

After 48 hours, a fraction of the NHK cell supernatant was removed. Each sample of supernatant (2 times 100 µl) from a well on the NHK plate (24 wells) was transferred to two wells in the NHF plate already containing 100 µl of E-199 medium per well. This gave a final volume of 200 µl/well (50:50 ratio of KSFM/E-199 medium) which remained on the NHF cells for 48 hours.

5. Measurement of Proliferation

Cell proliferation was quantified by the method described in the "Cell Proliferation ELISA, BrdU" kit (Roche Applied Science No. 11669915001). This is an immunological assay with luminescence detection (Genios, Tecan).

6. Expression of Results

The means of the luminescence values (RLU/s) of six wells with the same treatment condition were determined. These means were compared with the mean for the six control wells (Student t test–comparison of means–significant difference at 95% if $p<0.05^*$ and at 99% if $p<0.01^{**}$).

Proliferation of treated cells was expressed as a percentage of the control(untreated cells–100%) (OD treated/OD control×100).

For the conditions Vitamin A propionate+/−NAG6P (transferred), the percent proliferation was expressed relative to the DMSO control (1:10,000 dilution corresponding to the amount of DMSO actually present) in place of the Control.

The results shown in Table 9 below correspond to the mean of six wells into which six NHK supernatants were transferred.

TABLE 9

Fibroblast proliferation after 48 hours - effect of NAG6P alone or in combination with vitamin A propionate

|  | RLU | % Proliferation |
|---|---|---|
| Control | 4121 ± 205 | / |
| NAG6P 10 mM | 4903 ± 377 | 119%** |
| NAG6P 5 mM | 4985 ± 184 | 121%** |
| DMSO control* | 4240 ± 187 | 100% |
| Vit. A propionate 1 µM | 4640 ± 267 | 109%** |
| NAG6P 10 mM + Vit. A propionate 1 µM | 5693 ± 391 | 134%** |

[a]DMSO control: 1:10,000 dilution corresponding to amount of DMSO present in the treatment with vitamin A propionate and the combination NAG 10 mM + Vit. A propionate 1 µM.
*Student test: p < 0.05 - result significant at 95%
**Student test: p < 0.01 - result significant at 99%

Conclusions:

After incubating keratinocytes for 48 hours in the presence of NAG6P alone, then transferring the supernatant of these cells onto fibroblasts, it was observed in a surprising manner that there was a significant increase in fibroblast proliferation. Even more surprisingly, this increase was not related to the NAG6P concentration used in the keratinocyte pre-incubation, indicating that it is probably not the NAG6P that could act directly on fibroblast proliferation. Therefore, NAG6P most certainly induces a response of keratinocytes which, under the effect of this compound, secrete one or more molecules (probably hyaluronic acid of different sizes) in their supernatant, which in turn activate fibroblast proliferation.

In a remarkable manner, the combination of NAG6P and vitamin A propionate led to a greater stimulation of fibroblast proliferation than either product tested separately.

NAG6P is therefore able to induce fibroblast proliferation through the intermediary of keratinocytes, alone or in synergy with vitamin A propionate, and is therefore of interest for stimulating skin cell renewal.

Example 6: Test of the Effects of N-Acetylglucosamine-6-Phosphate on Human Skin

In this study, the effects of N-acetylglucosamine-6-phosphate were evaluated on living human skin and compared with the effects of the commercially available "RetinOx+ Day" cream containing retinol (0.02 to 0.05%). In particular, the following parameters were evaluated:

general skin morphology after staining with Masson trichrome,
acid glycosaminoglycan (GAG) content after alcian blue staining,
expression level of the hyaluronic acid CD44 receptor after immunolabeling of this receptor.

1. Product Tested

Product tested: N-acetylglucosamine-6-phosphate (NAG6P) at a concentration (w/v) of 1% (P1), 0.1% (P2) and 0.01% (P3).

2. Biological Model

Thirty-three explants (approximately 10 mm in diameter) were taken from a 36-year-old Caucasian woman (P712AB36) undergoing abdominoplasty. The explants were divided into 11 groups of three explants and placed in special skin explant survival medium.

| Group | No. of explants | Treatment | Sample | Evaluations |
|---|---|---|---|---|
| C D0 | 3 | None | D0 | Morphology GAG CD44 |
| C D6 | 3 | None | D6 | GAG CD44 |
| R D6 | 3 | RetinOx + Day Cream | D6 | GAG CD44 |
| P1 D6 | 3 | Active agent: NAG6P 1% | D6 | GAG CD44 |
| P2 D6 | 3 | Active agent: NAG6P 0.1% | D6 | GAG CD44 |
| P3 D6 | 3 | Active agent: NAG6P 0.01% | D6 | GAG CD44 |
| C D10 | 3 | None | D10 | Morphology GAG CD44 |
| R D10 | 3 | RetinOx + Day Cream | D10 | Morphology GAG CD44 |
| P1 D10 | 3 | Active agent: NAG6P 1% | D10 | Morphology GAG CD44 |
| P2 D10 | 3 | Active agent: NAG6P 0.1% | D10 | Morphology GAG CD44 |
| P3 D10 | 3 | Active agent: NAG6P 0.01% | D10 | Morphology GAG CD44 |

3. Treatment

RetinOx+Day cream was applied on the explants at 1 mg/cm² on days D0, D2, D3, D6 and D8.

On D0, D2, D3, D6 and D8, 30 μA of products P1, P2 and P3 were deposited on filter paper disks placed on the explants.

Controls did not receive any treatment.

4. Samples

On D0, the three explants in group C0 were sampled and cut in two. One-half was fixed in ordinary Bouin's solution and the other half stored at −80° C. On D6 and D10, three explants from each group were sampled and treated in the same manner.

5. Histology

After 48 hours of fixing in ordinary Bouin's solution, samples were dried and impregnated in paraffin using a Leica 1020 automated tissue processor, then embedded according to operating procedure MO-H-153 using a Leica EG 1160 embedding station. 5 μm sections were prepared according to operating procedure MO-H-173 using a Leica RM 2125 Minot microtome and mounted on Superfrost® histologic glass microscope slides.

5.1 General Morphology

General morphology was studied on paraffin sections stained with Masson trichrome, Goldner variant, according to operating procedure MO-H-157.

5.2 Visualization of Acid GAG

Acid GAGs were visualized with alcian blue staining. They were present throughout the papillary dermis.

In this zone, the GAGs under study are stained blue and correspond to acid GAGs.

The intensity of staining was quantified by image analysis.

5.3 CD44 Immunolabeling

Frozen sections were labeled for the CD44 receptor using mouse anti-CD44 monoclonal antibody (Invitrogen MHC D4400) at 1:100 dilution incubated for 1 hour at room temperature with a biotin/streptavidin amplifier system with FITC. Nuclei were counterstained with propidium iodide.

Results

General Morphology

At Day D0:

The stratum corneum of the explants was moderately thickened, very moderately laminated, and fully keratinized at its surface and base. The epidermis had 5 to 6 cell strata with good morphology. The dermal-epidermal junction had a moderate relief. The papillary dermis had fairly thick collagen fibers forming a rather dense network, with good cellularity.

Figure 2:
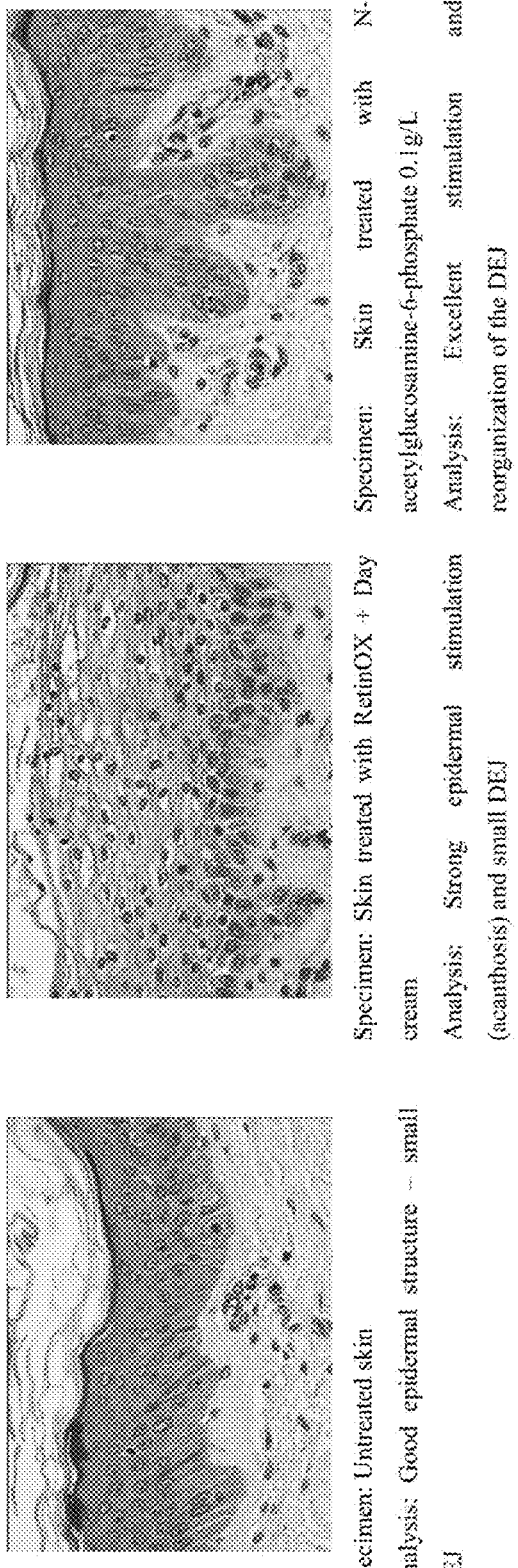
FIG. 2 presents an analysis of skin morphology after treatment with N-acetylglucosamine-6-phosphate.

At Day D10 (See FIG. 2):

The structure of the epidermis and dermis of the control explants was slightly altered, with marked keratinization at the base of the stratum corneum and mild parakeratosis. Basal layers showed mild spongiosis.

Application of the RetinOx+Day reference cream led to a very distinct retinoic type of reaction with very marked epidermal acanthosis (5 to 6 cell strata/19 to 20). The papillary dermis was dense.

Application of NAG6P on the explants resulted in considerable modifications of epidermal morphology. In particular, application of 0.01% NAG6P (product P3) led to changes in general morphology and a clear reorganization/strengthening of the dermal-epidermal junction. The papillary dermis was more or less dense.

Visualization/Quantification of Acid GAGs

Visual Analysis

At Day D0:

Acid GAGs were moderate throughout the papillary dermis and clearly seen in the fibroblasts.

At Day D6 (See FIG. 3):

On untreated explants, GAGs were expressed at a slightly greater extent than at C0.

With RetinOx+Day cream, they were moderate and fairly dense along the dermal-epidermal junction (DEJ) and in the rest of the papillary dermis.

With NAG6P, they were moderate along the DEJ and present throughout the papillary dermis, in a dose-dependent manner: acid GAGs were denser with 1% NAG6P than with 0.01%.

At Day D10:

On untreated explants, GAGs were similar to those seen at D6.

With the reference RetinOx+Day cream, they were distinct and fairly dense along the dermal-epidermal junction (DEJ) and in the rest of the papillary dermis.

With NAG6P, the effect seen at D6 was confirmed: acid GAGs were moderately present along the DEJ and throughout the papillary dermis, in a dose-dependent manner: acid GAGs were denser with 1% NAG6P than with 0.01%.

Quantitative Analysis

Acid GAGs were quantified by image analysis. The results are expressed as the percentage of the analyzed area in Table 10 below.

TABLE 10

Percentage of area occupied by acid GAGs in the papillary dermis

| | D0 | | D10 | |
|---|---|---|---|---|
| % of analyzed area | Mean | SD | Mean | SD |
| Control explants | 37.9 | 11.6 | 11.4 | 5.7 |
| Explants treated with RetinOx + Day cream | / | / | 23.8 | 8.7 |
| Explants treated with NAG6P 1% | / | / | 21.0 | 3.4 |
| Explants treated with NAG6P 0.1% | / | / | 16.3 | 6.3 |
| Explants treated with NAG6P 0.01% | / | / | 14.0 | 4.0 |

Expression of the Hyaluronic Acid CD44 Receptor

At Day D0:

CD44 expression was clear and very regular in the explants.

In the epidermis, CD44 was more or less punctiform, with membrane and pericellular location in all the living layers to the granular layer. In the papillary dermis, it was very distinct on fibroblasts and on fine fibers.

At Day D6:

In the untreated explants, CD44 expression decreased in both the epidermis and the papillary dermis.

In the group treated with RetinOx+Day cream, CD44 was moderately overexpressed.

CD44 was mildly overexpressed in the group treated with 1% and 0.1% NAG6P; this overexpression was very moderate with 0.01% NAG6P.

At Day D10 (See FIG. 4):

In the untreated explants, CD44 was slightly overexpressed, especially in the basal epidermis and papillary dermis.

In the group treated with RetinOx+Day cream, CD44 was moderately overexpressed.

This overexpression was very clear with 0.01% NAG6P in both the epidermis and papillary dermis.

Conclusions

This study showed, in a remarkable manner, that application of N-acetylglucosamine-6-phosphate on human skin induced several phenomena:

a visible reorganization of the dermal-epidermal structure with a clear reinforcement of the dermal-epidermal junction, without acanthosis, in contrast to RetinOx+Day cream;

an increase in acid GAG content (thus, mainly hyaluronic acid which is the main acid GAG in skin), not only at the dermal-epidermal junction as with RetinOx+Day cream, but well distributed throughout the papillary dermis;

an increase in the levels of the hyaluronic acid CD44 receptor, indicating hyaluronic acid synthesis activity and activation of skin cells.

Notably, this compound alone was as effective or even more so than a commercial retinol cream (for example, unlike the commercial cream, N-acetylglucosamine-6-phosphate does not cause acanthosis).

N-acetylglucosamine-6-phosphate is therefore of interest for stimulating several phenomena in the skin:

replumping the skin by stimulating the synthesis of GAGs, components of the three-dimensional support matrix of the skin, enhancing nutrient exchange between the epidermis and dermis by improving the dermal-epidermal junction, smoothing and tightening the skin by improving the dermal-epidermal junction and stimulating GAG synthesis, promoting skin regeneration by stimulating the CD44 receptor.

Example 7: Examples of Skin Care Compositions Containing N-Acetylglucosamine-6-Phosphate (NAG6P)

6.1 Regenerating Cream for Mature Skin
A—Aqueous Phase

| | |
|---|---|
| Glycerin | 2.0% |
| Hexylene glycol | 3.0% |
| Xanthan gum | 0.5% |
| Preservatives | qs |
| Carbomer | 0.35% |
| NAG6P | 0.1% |
| Water | qsp.100% |

B—Fat Phase

| | |
|---|---|
| Squalane | 15% |
| Cetyl alcohol | 2% |
| Arachidyl alcohol/behenyl alcohol/arachidylglucoside) | 1% |
| Glycerol stearate | 5% |
| Water | 1.5% |
| NaOH | 0.35% |
| Preservative + fragrance | qs |

6.2. Moisturizing and Emollient Emulsion
A—Fat Phase

| | |
|---|---|
| Ceteareth-2 | 3.5% |
| Ceteareth-21 | 2 to 4% |
| Wheat germ oil | 3% |
| Cyclomethicone | 7% |
| Octyl Palmitate | 8% |

B—Aqueous Phase

| | |
|---|---|
| Water | qsp.100% |
| Glycerin | 7.0% |
| Hexylene glycol | 3.0% |
| NAG6P | 0.1% |
| Preservatives | qs |

C—Ingredients Added to the Emulsion at a Temperature Below 40° C.

| | |
|---|---|
| Sodium hyaluronate | 0.1% |
| Water | 5% |
| Tocopherol | 0.05% |
| Vitamin A palmitate | 0.1% |
| Phospholipids | 0.5% |
| Ceramides 3 | 0.1% |
| Polyacrylamide & $C_{14-13}$ isoparaffin & laureth-7 | 2 to 3.5% |

6.3. Sun Cream for Photoaged Skin
A—Fat Phase

| | |
|---|---|
| Glycerol monostearate | 2% |
| PEG-100 stearate | 3% |
| C12-C15 alkyl benzoate | 10% |
| Dimethicone | 5% |
| Tocopherol acetate | 1% |
| Octyl-triazone (Uvinul T150) | 1.5% |
| Butyl Methoxy Dibenzoyl methane (Eusolex 9020) | 2.0% |
| Cetostearyl alcohol | 1% |

B—Aqueous Phase

| | |
|---|---|
| Water | qsp.100% |
| Preservatives | 0.6% |
| Glycerin | 7% |
| Hexylene glycol | 3.0% |
| Carbomer | 0.5% |
| Tetrasodium EDTA | 0.2% |
| NAG6P | 0.1% |
| Sodium hyaluronate HMW | 0.1% |
| Water | 5% |
| NaOH | 0.5% |
| Preservative + fragrance | qs. |

6.4. Anti-Wrinkle Cream, Post-Injection <<Filler>>
A—Fat Phase

| | |
|---|---|
| Squalane | 5% |
| Cetyl alcohol | 2% |
| Dimethicone | 5% |
| Octyl palmitate | 5% |

B—Aqueous Phase

| | |
|---|---|
| Butylene glycol | 0.5-4% |
| Water | qsp.100% |
| NAG6P | 0.1% |
| Glycerin | 2.0% |
| Hexylene glycol | 3.0% |
| Xanthan gum | 0.5% |
| Preservatives | qs |

C—Ingredients Added to the Emulsion at a Temperature Below 40° C.

| | |
|---|---|
| Tocopherol acetate | 0.1 to 1% |
| Pyridoxine | 0.01 to 0.05% |
| Vitamin A palmitate | 0.01 to 1% |
| d-Panthenol | 0.1 to 1% |

-continued

| | |
|---|---|
| Citric acid | 0.1 to 0.5% |
| Zinc gluconate | 0.1 to 1% |
| Trisodium citrate | 1 to 2.5% |
| Water | 5% |

6.5. Make-Up Remover Lotion for Mature Skin

| | |
|---|---|
| Polysorbate 20 | 1.0% |
| Caprylyl/capryl glucoside (Oramix CG110) | 2.0% |
| NAG6P | 0.1% |
| PEG-7 glyceryl cocoate | 0.5% |
| Hexylene glycol | 4-5% |
| d-Panthenol | 0.1% |
| Mannitol | 0.02% |
| Preservatives | qs |
| Water | qsp.100% |

The invention claimed is:

1. A method of treating skin, the method comprising the administration of a cosmetic composition comprising N-acetylglucosamine-6-phosphate or a cosmetically acceptable salt thereof as an active ingredient and, optionally, a compound of the vitamin A family to skin in an amount effective to tighten skin, treat dry skin, treat aging skin, reduce wrinkles, reduce the appearance of fine lines, regenerate or strengthen dermal-epidermal junctions, enhance skin cell proliferation, enhance synthesis of structural macromolecules or improve skin tone.

2. The method of claim 1, wherein said composition further comprises a compound of the vitamin A family.

3. The method of claim 2, wherein said compound of the vitamin A family is selected from the group consisting of retinol, cis or trans retinal or cis or trans retinaldehyde, retinoic acid, isotretinoin, adapalene, tretinoin, salts thereof and a mixture thereof.

4. The method of claim 1, wherein said composition further comprises retinol, a salt thereof, an alcohol thereof or an ester thereof.

5. The method of claim 1, wherein said composition is in the form of a composition for topical administration, a composition for oral administration or a composition for injection.

6. The method of claim 5, wherein said composition is in a form suitable for topical administration.

7. The method of claim 1, the method comprising the administration of the cosmetic composition comprising N-acetylglucosamine-6-phosphate or a cosmetically acceptable salt thereof as an active ingredient and, optionally, a compound of the vitamin A family to skin in an amount effective to regenerate or strengthen dermal-epidermal junctions, enhance skin cell proliferation, enhance synthesis of structural macromolecules or improve skin tone.

8. The method of claim 2, wherein the compound of the vitamin A family is used at a concentration between 3 µg/L and 10 mg/L or between 3 µg/kg and 10 mg/kg of the composition.

9. A method of treating skin, the method comprising administering to skin a cosmetic composition consisting of:
 a) N-acetylglucosamine-6-phosphate or a cosmetically acceptable salt thereof as an active ingredient, and
 b) optionally, a compound of the vitamin A family or a cosmetically acceptable salt, alcohol, or ester thereof,
 wherein the cosmetic composition is administered in an amount effective to tighten skin, treat dry skin, treat aging skin, reduce wrinkles, reduce the appearance of fine lines, regenerate or strengthen dermal-epidermal junctions, enhance skin cell proliferation, enhance synthesis of structural macromolecules or improve skin tone.

10. The method of claim 9, wherein said composition consists of:
 a) N-acetylglucosamine-6-phosphate or the cosmetically acceptable salt thereof as an active ingredient, and
 b) the compound of the vitamin A family or the pharmaceutically acceptable salt, alcohol, or ester thereof.

11. The method of claim 10, wherein said compound of the vitamin A family is selected from the group consisting of retinol, cis or trans retinal or cis or trans retinaldehyde, retinoic acid, isotretinoin, adapalene, tretinoin, salts thereof and a mixture thereof.

12. The method of claim 10, wherein the compound of the vitamin A family is retinol, a salt thereof, an alcohol thereof or an ester thereof.

13. The method of claim 9, wherein said composition is in the form of a composition for topical administration, a composition for oral administration or a composition for injection.

14. The method of claim 13, wherein said composition is in the form of a composition for topical administration.

15. The method of claim 9, wherein the cosmetic composition is administered in an amount effective to regenerate or strengthen dermal-epidermal junctions, enhance skin cell proliferation, enhance synthesis of structural macromolecules or improve skin tone.

16. The method of claim 10, wherein the compound of the vitamin A family is at a concentration between 3 µg/L and 10 mg/L or between 3 µg/kg and 10 mg/kg of the composition.

* * * * *

UNITED STATES PATENT AND TRADEMARK OFFICE
CERTIFICATE OF CORRECTION

PATENT NO. : 9,907,760 B2
APPLICATION NO. : 13/637031
DATED : March 6, 2018
INVENTOR(S) : Daniel Auriol et al.

Page 1 of 1

It is certified that error appears in the above-identified patent and that said Letters Patent is hereby corrected as shown below:

In the Specification

Column 12,
Line 37, "220 µA" should read --220 µl--.
Line 40, "(≈ 350 µA)" should read --(≈ 350 µl)--.

Column 23,
Line 1, "30 µA" should read --30 µl--.

Signed and Sealed this
Twenty-third Day of July, 2019

Andrei Iancu
*Director of the United States Patent and Trademark Office*